(12) United States Patent
Brouwers (10) Patent No.: US 11,298,650 B2
(45) Date of Patent: Apr. 12, 2022

(54) ROTATIONAL ABSORBER DEVICE AND METHOD FOR SCRUBBING AN ABSORBATE FROM A GAS

(71) Applicant: Romico Hold A.V.V., Oranjestad (AW)

(72) Inventor: Jozef Johannes Hubertus Brouwers, Lanaken (BE)

(73) Assignee: Romico Hold A.V.V., Oranjestad (AW)

( * ) Notice: Subject to any disclaimer, the term of this patent is extended or adjusted under 35 U.S.C. 154(b) by 181 days.

(21) Appl. No.: 16/614,031

(22) PCT Filed: May 1, 2018

(86) PCT No.: PCT/NL2018/050286
§ 371 (c)(1),
(2) Date: Nov. 15, 2019

(87) PCT Pub. No.: WO2018/212643
PCT Pub. Date: Nov. 22, 2018

(65) Prior Publication Data
US 2020/0070089 A1  Mar. 5, 2020

(30) Foreign Application Priority Data

May 16, 2017 (NL) ..................................... 2018925

(51) Int. Cl.
*B01D 53/18* (2006.01)
*B01D 53/14* (2006.01)
*C07C 31/04* (2006.01)

(52) U.S. Cl.
CPC ....... *B01D 53/185* (2013.01); *B01D 53/1406* (2013.01); *B01D 53/1481* (2013.01); *B01D 53/1487* (2013.01); *C07C 31/04* (2013.01)

(58) Field of Classification Search
CPC ........ B01D 3/28; B01D 3/30; B01D 53/1481; B01D 53/1487; B01D 53/185;
(Continued)

(56) References Cited

U.S. PATENT DOCUMENTS 2,662,759 A   12/1953   Brewer
3,486,743 A   12/1969   Todd
(Continued)

FOREIGN PATENT DOCUMENTS

CH          608192 A5    12/1978
CN      101234261 A  *   8/2008  ............... B01D 3/30
(Continued)

OTHER PUBLICATIONS

CN101234261A_ENG (Espacenet machine translation of Ji) (Year: 2008).*

*Primary Examiner* — Jonathan Miller
*Assistant Examiner* — Gabriel E Gitman
(74) *Attorney, Agent, or Firm* — The Webb Law Firm (57) ABSTRACT

A device and method for scrubbing an absorbate from a gas is described. The rotational absorber device comprises a housing having a gas inlet, a gas outlet, an absorbent liquid inlet and an absorbent liquid outlet; a rotor mounted for rotation in said housing and connecting to the inlets and outlets, the rotor comprising a plurality of scrubbing channels extending axially and parallel to a common rotation axis; and means for rotating the rotor. The device and method provide a scrubbing of the gas with improved selectivity and efficiency.

11 Claims, 4 Drawing Sheets

(58) Field of Classification Search
CPC .... B01D 19/0052; B01D 45/12; B01D 53/18; B01D 53/14; B01D 53/1406; B01J 19/18; B01J 19/28; C07C 31/04
See application file for complete search history.

(56) References Cited

U.S. PATENT DOCUMENTS

| | | | |
|---|---|---|---|
| 4,181,675 A * | 1/1980 | Makin | B01D 53/22 518/705 |
| 5,667,543 A * | 9/1997 | Brouwers | B01D 45/14 55/317 |
| 2012/0198999 A1 | 8/2012 | e Mello et al. | |
| 2014/0047979 A1* | 2/2014 | Eimer | C10L 3/102 95/151 |
| 2016/0332113 A1* | 11/2016 | Jenkins | B01D 53/502 |

FOREIGN PATENT DOCUMENTS

| | | |
|---|---|---|
| CN | 101234261 A | 8/2008 |
| CN | 101791510 A | 8/2010 |
| CN | 101890250 A | 11/2010 |
| JP | H09220435 A | 8/1997 |
| NL | 7608232 A | 1/1978 |
| WO | 2012092981 A1 | 7/2012 |

* cited by examiner

ROTATIONAL ABSORBER DEVICE AND METHOD FOR SCRUBBING AN ABSORBATE FROM A GAS

CROSS-REFERENCE TO RELATED APPLICATIONS

This application is the United States national phase of International Application No. PCT/NL2018/050286 filed May 1, 2018, and claims priority to Dutch Patent Application No. 2018925 filed May 16, 2017, the disclosures of which are hereby incorporated by reference in their entirety.

TECHNICAL FIELD

The present invention concerns a rotational absorber device for scrubbing an absorbate from a gas. The invention further relates to a method for scrubbing an absorbate from a gas.

BACKGROUND ART

Scrubbing a waste gas from unwanted components (the absorbate) has been performed since long. Typical scrubbing treatment installations bring a gas stream into contact with a so-called absorbent liquid with the aim of allowing the absorbate in the form of certain gaseous components to pass from the gas to the liquid. Scrubbing can for instance be used to limit emissions. Scrubbing is also referred to as absorption in the art.

During scrubbing a transfer of components from the gas to the absorbent liquid occurs. The level of gaseous components that actually passes to the absorbent liquid is among other factors determined by the ability of the absorbate to dissolve in the absorbent liquid. Henry's Law is applicable to the solubility of gases in liquids, for low concentrations and components with a partial pressure<1 atm:

$$p = H \cdot x$$

wherein
p=partial pressure (Pa)
x=mole fraction
H=Henry constant (Pa)

This allows one to calculate the maximum concentration of an absorbate in the absorbent liquid for any desired end concentration.

Conventional ways of scrubbing a gas are by liquid spraying, wetted tray columns and wetted packed columns. Although the known devices may operate satisfactorily, they are prone to improvements, in particular regarding their efficiency. Efficiency for instance may relate to the amount of absorbent liquid that is needed to take up a certain amount of absorbate.

U.S. Pat. No. 2,662,759 discloses a multicellular fractionation device. Its purpose is to fractionate an incoming medium into different components, which is quite different from scrubbing which purpose indeed is to remove components from a gas by dissolving these components in a separately added liquid. Fractionating and scrubbing are different unit operations of process technology, and their physics differs substantially which entails differences in design and operational procedures. The column of U.S. Pat. No. 2,662,759 comprises axially arranged rotating elements and stationary plates between them, both of these being provided with channels. Rotation is thus followed by non-rotation in a number of axially subsequent stages whereby each stage is the equivalent of a tray in a classical fractionating column. The configuration is said to enhance radial mixing to reduce horizontal inhomogeneity in concentrations and temperatures. Reaching stage equilibrium is indeed a desired feature of a fractionating column. However, the arrangement of rotating and non-rotating elements makes the device of U.S. Pat. No. 2,662,759 unsuitable for scrubbing. The vertical space between each rotating and non-rotating element provides a gap through which an absorbent liquid would be transported in a radial direction as a result of the centrifugal forces acting on the liquid. Introduced absorber liquid thus would move more and more to a radially outer part of the column with vertical distance from an upstream end (a top end) of the device. This would cause an inhomogeneous distribution of the absorbent liquid over the channels, and the desired scrubbing would not occur.

It is an aim of the present invention to provide an absorber device for scrubbing an absorbate from a gas having an improved efficiency over the state of the art device. It is a further aim to provide a more compact absorber device for scrubbing an absorbate from a gas. Yet another aim is to provide a more efficient method for scrubbing an absorbate from a gas.

SUMMARY OF THE INVENTION

These and other aims are provided by a rotational absorber device for scrubbing an absorbate from a gas, the device comprising a housing having a gas inlet, a gas outlet, an absorbent liquid inlet and an absorbent liquid outlet; a rotor mounted for rotation in said housing and connecting to the inlets and outlets, the rotor comprising a plurality of scrubbing channels extending axially and parallel to a common rotation axis; and means for rotating the rotor. The channels are circumferentially enclosed by walls over an entire axial length of the rotor between the absorbent liquid inlet and the absorbent liquid outlet; and the device further comprises means for providing a sustained flow of absorbent liquid to the absorbent liquid inlet.

The invented device allows to efficiently absorbing an absorbate from a gas. Thereto, a method in accordance with the invention aimed at scrubbing an absorbate from a gas comprises providing a rotational absorber device in accordance with the invention, feeding a gas to the gas inlet, feeding an absorbent liquid to the absorbent liquid inlet, rotating the rotor in said housing which causes the absorbent liquid to confine to an inward facing wall of the scrubbing channels and form a film thereto, allowing molecular transport of absorbate from the gas to the absorbent liquid, and exiting the gas through the gas outlet and the absorbent liquid through the absorbent liquid outlet. The gas that enters the housing and the scrubbing channels of the rotating rotor contains a compound referred to as absorbate which is absorbed by the liquid referred to as absorbent or absorbent liquid. In a typical operation, the film that is formed on the channel walls absorbs at least part of the absorbate, and the film containing (part of) the absorbate in an embodiment flows parallel to the gas in the scrubbing channels and eventually breaks up in droplets when leaving the channels. Due to the rotation of the rotor, the absorbent liquid droplets are propelled radially outwards with respect to a central axis of rotation of the rotor towards the absorbent liquid outlet of the housing where the liquid is discarded and/or collected.

The invented rotational absorber device has the advantage that it may be designed relatively small in size, in particular relative to known absorber devices, such as spray towers for instance. The small size is achieved by providing the plurality of preferably parallel channels of small size in the rotor. The cross-sectional size of the scrubbing channels may be selected within a large region, depending on the specific application. Suitable cross-sectional widths of the channels may be as small as 1 mm, or even 0.1 mm, and preferably are limited to 10 mm, more preferably to 5 mm. Because of rotation of the rotor, the absorber liquid will migrate towards and eventually be confined to an inward facing wall of each channel, where it forms a film with a thickness that may be as small as 0.001 to 1 mm, more preferably between 0.010 and 0.1 mm. The small cross-sectional width of the channels and the small thickness of the film promotes a low resistance to molecular transport of absorbate from gas to absorbent liquid.

A further advantageous effect of the rotating rotor is that the absorbent liquid is at least partly separated in the form of droplets that are propelled towards the liquid outlet. This rotation caused separation avoids having to install a separate liquid separator downstream of the actual absorber device, as is typically done in the prior art.

The result of using the invented device is a compact and effective system for removing constituents (absorbate) in gases by absorption. The invented device can also be used to cool down gases and to remove condensed components which are absorbed in the liquid film.

Due to the action of the centrifugal force liquid and gas that are brought into rotation when passed through a scrubbing channel of the rotor moves radially, away from the axis of rotation towards a radial boundary which extends parallel to the axis of rotation and forms a boundary of the channels in the rotor. The outer boundary of the scrubbing channels serves as a means for collecting those liquid parts that were able to reach and settle at this boundary and which can subsequently be removed from the gas flowing parallel along the collecting boundary. The extent to which liquid can reach the collecting boundary and act to absorb gas absorbate can be assessed from the time for a liquid molecule to reach the collecting boundary in combination with the residence time, the time for the gas to pass through the channel. One skilled in the art will be able to adopt a suitable axial velocity of the gas in order to achieve the desired effect of liquid film forming and absorption of gas constituents. A suitable axial extent of the rotor and the scrubbing channels may be as large as 100-5000 times the cross-sectional width of the channels.

The gas and the liquid in an embodiment of the rotational absorber device are inserted upstream of the rotor, whereto the device is provided with a gas inlet and an absorbent inlet both located upstream of the rotor. The gas and the absorbent liquid in this embodiment flow in the same direction, i.e. exhibit co-current flow. It may also be possible to define the flow direction of the gas in relation to the liquid differently. In an embodiment of counter-flow, the absorbent liquid and the to-be-cleaned gas flow in opposite directions. The main advantage of counter-flow scrubbing is that the cleaner the gas becomes, the lower the pollutant concentration in the absorbent liquid will be.

In another embodiment of the rotational absorber device the gas outlet and the absorbent liquid outlet are located downstream of the rotor.

The amount of scrubbing channels may be chosen within a wide range, depending on the application. A suitable embodiment of the rotational absorber device comprises an amount of scrubbing channels of at least 10, more preferably at least 100, and most preferably at least 1000. Increasing the amount may increase efficiency at the expense of pressure drop across the rotor. Combining a large number of channels in one rotating rotor provides a means for handling large amounts of gas to be cleaned.

The channels may be provided in the rotor in any possible way, for instance by perforating a massive cylinder with the desired amount of channels, arranged parallel to the rotation axis of the cylinder. Another possibility is to provide a plurality of narrowly spaced concentric cylinders and each annulus between two adjacent cylinders is divided by at least one azimuthally placed axially extending partition. Other means of making the rotor may also be envisaged.

The channels are entirely circumferentially enclosed by walls over the entire axial length of the rotor between the absorbent liquid inlet and outlet. Absence of holes or openings in the channel walls effectively prevents absorber liquid of leaking in a radial direction due to the action of the centrifugal force. It supports maintaining a homogeneous distribution of absorber liquid over the whole length of the rotating element. At the bottom (downstream) end, the centrifugal force acts as a means to propel absorbent liquid radially upon leaving the rotating element or rotor. Liquid loaded by absorbate is thus effectively separated from the gas which, depending on the way of operation, enters or leaves the rotating element or rotor at the bottom (downstream) end.

The means for providing a sustained flow of absorbent liquid to the absorbent liquid inlet may comprise a pump, or may be provided by the water supply system for instance, in case the absorbent liquid comprises water.

The introduced absorbent fluid develops a fluid film at the collecting boundary of each scrubbing channel. If the rotating rotor is installed with its axis of rotation vertically, collected fluid will preferably not flow downwards as a result of gravity but will preferably be entrained by the gas flow in the scrubbing channels due to shear forces. The level of shear force in the channels can be influenced by the pressure gradient in the scrubbing channels. This pressure gradient may be determined by the pressure of the upstream gas, i.e. the pressure of the gas at the gas inlet.

To be able to increase shear force in the channels to any preferred level, an embodiment of the invention relates to a device which further comprises pressurizing means for the inlet (fed) gas. In a corresponding embodiment of the method, the inlet (fed) gas is pressurized to a pressure of between 1 and 20 bar, more preferably of between 1 and 10 bar for best results.

Due to the centrifugal force, the liquid when leaving the rotor and the scrubbing channels thereof is propelled outwards. The rotation as such may not have a large effect on molecular transport and absorption. The rotation of the rotor however tends to hold the formed liquid film against channel walls and hinders or prevents this film from leaving said walls. The result is that apart from the absorption achieved, a good separation of gas and liquid is inherent to the absorption device. The liquid when exiting the channels therefore is well separated from the gas stream and can be collected. In the housing, means can be provided for continuous transportation of the absorbent fluid.

The channels are preferably provided substantially parallel to the axis of rotation. Application of collecting walls positioned non-parallel to the axis of rotation results in a component of the centrifugal force acting parallel to the collecting boundary and can serve as a means for or to enhance the continuous transportation of the collected fluid film along the channel walls. However, such inclined walls may cause secondary flows, in particular under laminar flow conditions, such as secondary flows due to Coriolis forces. These secondary forces may disturb the process of radial migration and settling of liquid particles. A small inclination in the order of 0.1-1 radians may be beneficial.

An embodiment of the rotational absorber device further comprises flow direction means provided upstream and/or downstream of the rotor, whereby the optionally upstream flow direction means act as means for rotating the rotor.

Suitable embodiments of the rotational absorber device have flow direction means comprising a volute, a stator blade or an impeller, or a combination of these. These may bring the inlet gas in rotation and minimize pressure losses over the device, in particular when providing driven flow direction means installed upstream and/or downstream of the scrubbing channels of the rotor. The flow direction means may in some embodiments act as means for rotating the rotor.

In order to effectively collect the absorbent liquid containing (part of) the absorbate, an embodiment of the rotational absorber device further comprises an absorbent liquid collector that connects to the absorbent liquid outlet. This collector is preferably provided within the housing of the device and may for instance be embodied as circumferential ridge or tray, provided against a side wall of the housing.

Because of the relatively small cross-sectional width of the channels in the rotor, the gas within the channels may exert a rather strong shear force on the liquid film deposited on the boundary walls of the channels. This may cause the liquid to flow in the same direction as the gas stream. Gas and liquid then flow in the same direction and a further improvement of absorption by such co-current flows may be achieved by preferred embodiments of the device in which rotors are provided in series. A suitable embodiment in this respect provides a rotational absorber device wherein the housing comprises a first and a second rotor both mounted for rotation in said housing whereby the second rotor is provided axially downstream from the first rotor.

The rotational absorber device according to an embodiment comprises a first and a second absorbent liquid inlet, located upstream of the first and second rotor respectively, whereas another embodiment that may be combined with the first embodiment comprises a first and a second absorbent liquid outlet, located downstream of the first and second rotor respectively.

In yet another embodiment of the rotational absorber device at least one of the first and second absorbent liquid outlets reconnects to at least one of the first and second absorbent liquid inlets, and a device wherein the second absorbent liquid outlet reconnects to the first absorbent liquid inlet is particularly preferred. In case of two rotors positioned in series with respect to each other, the gas exiting the first rotor enters the second rotor, while fresh absorbent liquid is fed to the second rotor. When leaving the second rotor, the partly used absorbent liquid is fed to the first rotor and leaves this rotor as more completely of even fully utilized absorbent liquid.

In operation, the concentration of the absorbate in the gas will reduce while the concentration of the absorbate in the liquid will increase. The equilibrium concentration in the gas, which corresponds to a certain concentration in the liquid, is determined by a number of factors comprising the temperature. The higher the temperature in the liquid, the higher the equilibrium concentration in the gas will be. Thus a reduction in temperature has a favourable effect on the yield of the rotational absorber device, which is preferably operated at temperatures below 50° C. more preferably below 40° C., more preferably at room temperature, and most preferably at a temperature below 10° C.

It is possible to increase the yield, i.e. the uptake of absorbate by the liquid, by adding chemicals to the absorbent liquid, which help to convert absorbed components. Thus adding chemicals that react with the absorbed gases has a positive effect on the absorption yield.

Besides water, organic liquids may be used as absorbent liquids. In appropriate cases chemicals or micro-organisms may be added to the absorbent liquid to convert or neutralise gases that are dissolved in the liquid. As a result of this conversion, the concentration in the liquid is reduced, which in-turn allows more gas to dissolve, according to Henry's Law.

The liquid-gas ratio in the rotational scrubbing device comprises the relation between the absorbent liquid flow rate and the gas stream flow rate. The invented device may require a lower amount of liquid per $m^3$ gas to realise a desired residual emission, as compared to conventional devices.

Although the centrifugally induced radial velocities of the fluid particles in the channels may be very small, small perturbations in the flow of the gas and liquid may be beneficial to the process of absorption of gaseous constituents as well as the liquid film formation at the outer boundary walls. An embodiment of the method wherein the hydraulic diameter of the scrubbing channels and the average axial gas velocity are selected such that the Reynolds number in the channels exceeds 1800, more preferably 2000, and the gas passes through the scrubbing channels in a (potentially) turbulent flow is therefore preferred. Turbulent flow is generally achieved when the Reynolds number of the flow through the channel is larger than 1800, preferably larger than 2000. The Reynolds number is well known and depends on the average axial velocity of the gas flow through a channel, the kinematic viscosity of the carrier gas and the hydraulic diameter of the channel. The hydraulic diameter may be determined according to well known principles and, for a circular channel cross-section is equal to its diameter. The average axial velocity of the gas can be influenced by the pressure gradient over the scrubbing channels. Prevailing turbulent flow in the scrubbing channels has been shown to improve absorption efficiency, possibly due to a better transport of gas molecules to the absorbent liquid. The shear forces acting on the liquid will under turbulent conditions increase relative to the shear forces under laminar conditions. The increased shear forces may cause co-current flow of the gas and the liquid, and an embodiment of the method in which turbulent and co-current flow of the gas and liquid occurs in the scrubbing channels is particularly preferred.

Turbulent gas flow in the channels will prevail when the Reynolds number is sufficiently large. For practically realistic values of flow velocity and channel diameter, a pressure in the channels of 2 or even 5 bar is needed to have a sufficiently large value of the gas density to end up with turbulent flow. At increased pressure and density combined with turbulent flow, the shear force acting by the gas on the liquid film will be large to the extent that gas and liquid flow occur in the same direction, at least partly. For a vertical position of the channels also, the force of gravity may not be large enough to result in a downward flow of liquid by gravity opposite to the upward flow of gas. Counter-current flow in the channels may then not be possible. On the other hand, at more moderate pressures of below 2 bar or 5 bar, the gas flow is prevailingly laminar and the shear force may no longer exceed the force of gravity. Counter-current operation may then be possible by injecting liquid at the top (upstream end of the device) which flows downward while gas which is injected at the bottom (downstream end of the device) flows upward. A fan may be provided in order to impose the required pressure difference necessary to induce the upward gas flow. In this embodiment, scrubbed gas leaves the rotor at the top and liquid loaded with absorbate leaves at the bottom.

It is explicitly mentioned that the embodiments disclosed in the present application may be combined in any possible combination of these embodiments, and that each separate embodiment may be the subject of a divisional application.

BRIEF DESCRIPTION OF THE FIGURES

The above brief description, as well as other objects, features and advantages of the present invention will be more fully appreciated by reference to the following detailed description of presently preferred, but nonetheless illustrative embodiments, when taken in conjunction with the accompanying drawings wherein.

DETAILED DISCLOSURE OF THE INVENTION

Figure 1A:
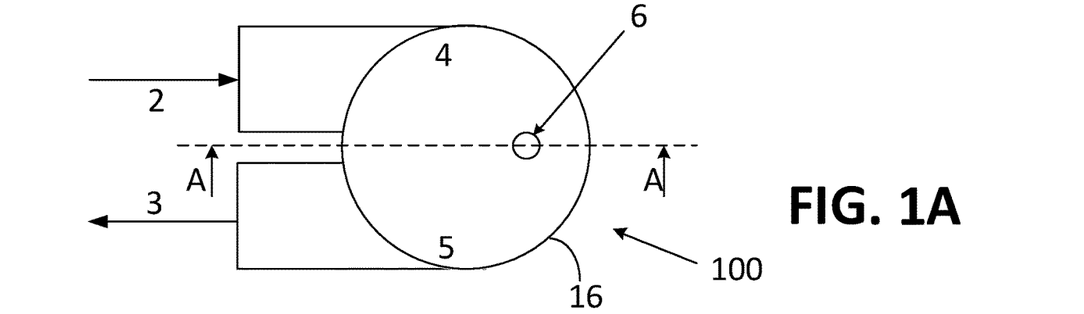
FIG. 1A is a schematic top view of a rotating absorber device according to an embodiment of the present invention.
Figure 1B:
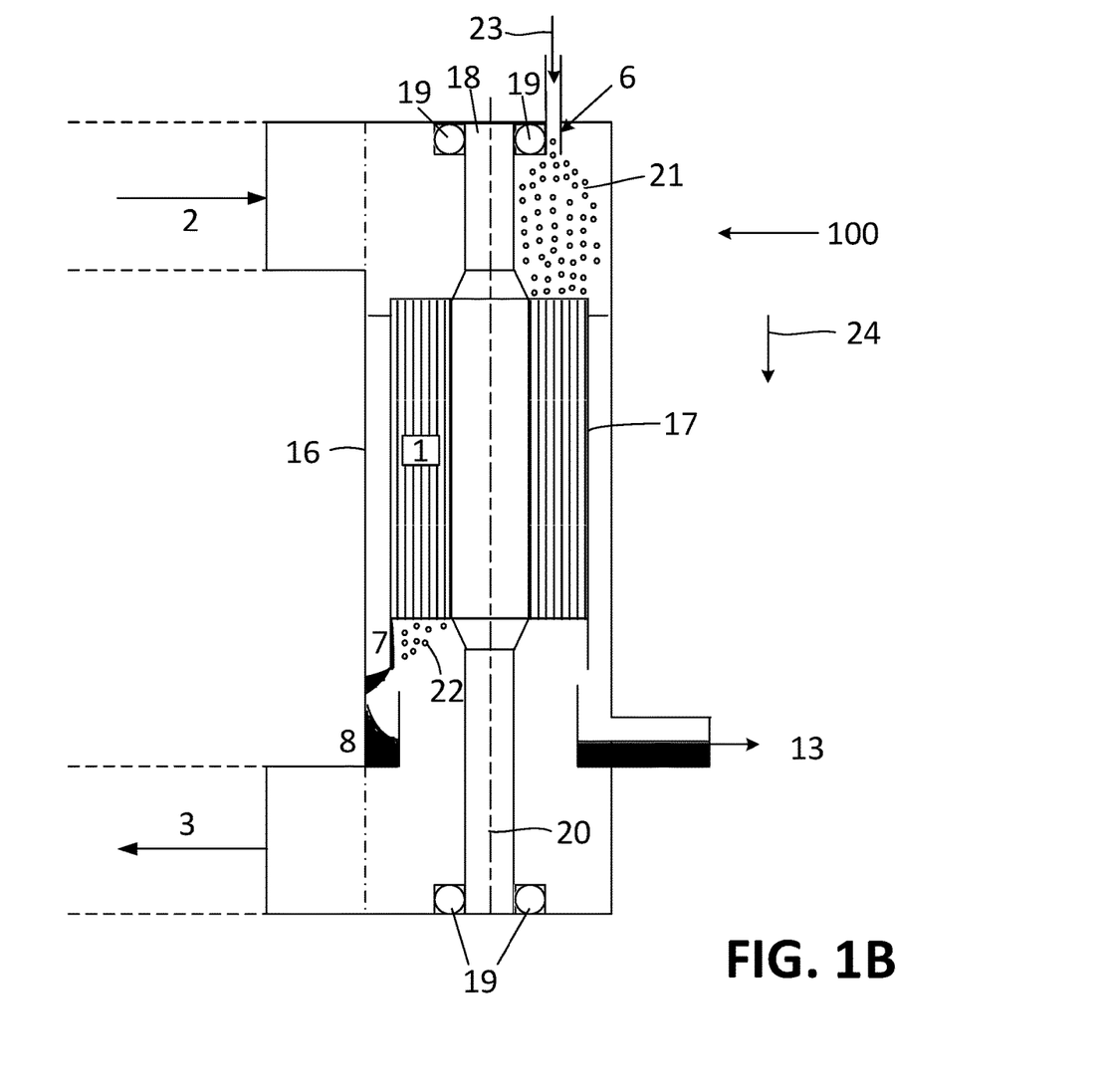
FIG. 1B is a schematic cross-sectional side view of a cross-section along a plane A-A of the embodiment shown in FIG. 1A.

Referring to FIGS. 1A and 1B, a rotating absorber device 100 according to an embodiment of the invention is shown. The device 100 comprises a cylindrical housing 16 in which a rotor 17 is mounted on a shaft 18 supported by bearings 19. The rotor 17 consists of a large number of axially extending scrubbing channels 1, arranged parallel to a rotation axis 20. The channels 1 are dimensioned such that a potentially turbulent flow may be achieved in the channels 1.

The rotor 17 is fixed to the shaft 18 which is rotatably mounted in the bearings 19, and which can be externally driven, if desired. Possible leakage between rotor 17 and housing 16 may be prevented by a suitable sealing arrangement. The housing 16 is provided with a gas inlet 2 and a gas outlet 3. The gas inlet 2 consists of a duct that is tangentially positioned at position 4 in the cylindrical housing 16 at an upstream end thereof to induce a swirling rotational motion of the incoming gas in the housing 16. The swirling gas motion induces a rotation of the rotor 17 within the housing 16 without any external driving means such as a rotational motor.

The gas outlet configuration 3 is a mirror image of the gas inlet configuration 2 and comprises a duct that is tangentially positioned at position 5 in the cylindrical housing 16 at a downstream end thereof to direct the outcoming gas from a swirling rotational motion into a translating motion while leaving the housing 16 at position 5.

Apart from the tangential inlets 2 and outlets 3, rotational gas motion can also be generated and nullified by stationary curved blades (not shown) provided at an upstream end and a downstream end of the rotor 17. The inner part of the static blade construction may contain the bearings 19 of the rotor 17.

On top of the housing 16 at the upstream end thereof, an inlet 6 for (fresh) absorbent liquid 21 is provided. In the embodiment shown, the liquid 21 is sprayed on top of the rotor 17 according to arrow 23 by a suitable spraying arrangement. The liquid 21 is sprayed on top of the rotor 17 whereby a rotation of the rotor around the axis 20 provides for an even distribution of liquid 21 over the channels 1. At the downstream side of the rotor 17, the absorber liquid 21 that now contains absorbate (denoted as absorbate-containing liquid 22) leaves the facing wall of a cylindrical shell 7 that forms an axial extension of the outer boundary wall of the rotor 17. At an inner side of the cylindrical shell 7 wall, a new film of absorbate-containing liquid 22 forms that breaks up at an outer end of the cylindrical shell 7 wall and is propelled as droplets to a liquid collection chamber 8 in the form of a cylindrical ridge provided inside the housing 16. The absorbent liquid leaves the housing 16 at outlet 13.

As an alternative to the vertical arrangement shown in FIGS. 1A and 1B, the rotational absorber device 100 according to an embodiment may be positioned horizontally. The flow of liquid 21 inside the channels 1 is controlled by centrifugal forces and shear forces exerted by the gas flowing inside the channels 1 of the rotor 17. When leaving the channels 1 of the rotor 17, the motion of the absorbate-containing liquid 22 and liquid droplets is governed by centrifugal forces. Gravitation becomes important only when the liquid flow is brought to rest in collection tanks (not shown) provided outside the rotational absorber device.

An external drive or engine may be used when there is a need to rotate the rotor 17 independently of the gas flow. Such means for rotating the rotor may in such an embodiment be connected to the rotor 17 through a magnetic coupling for instance. No shaft piercing through the housing 16 is needed in such embodiment, thus keeping the advantage of preventing the use of complicated sealing arrangements to prevent escape of gasses.

Figure 2:
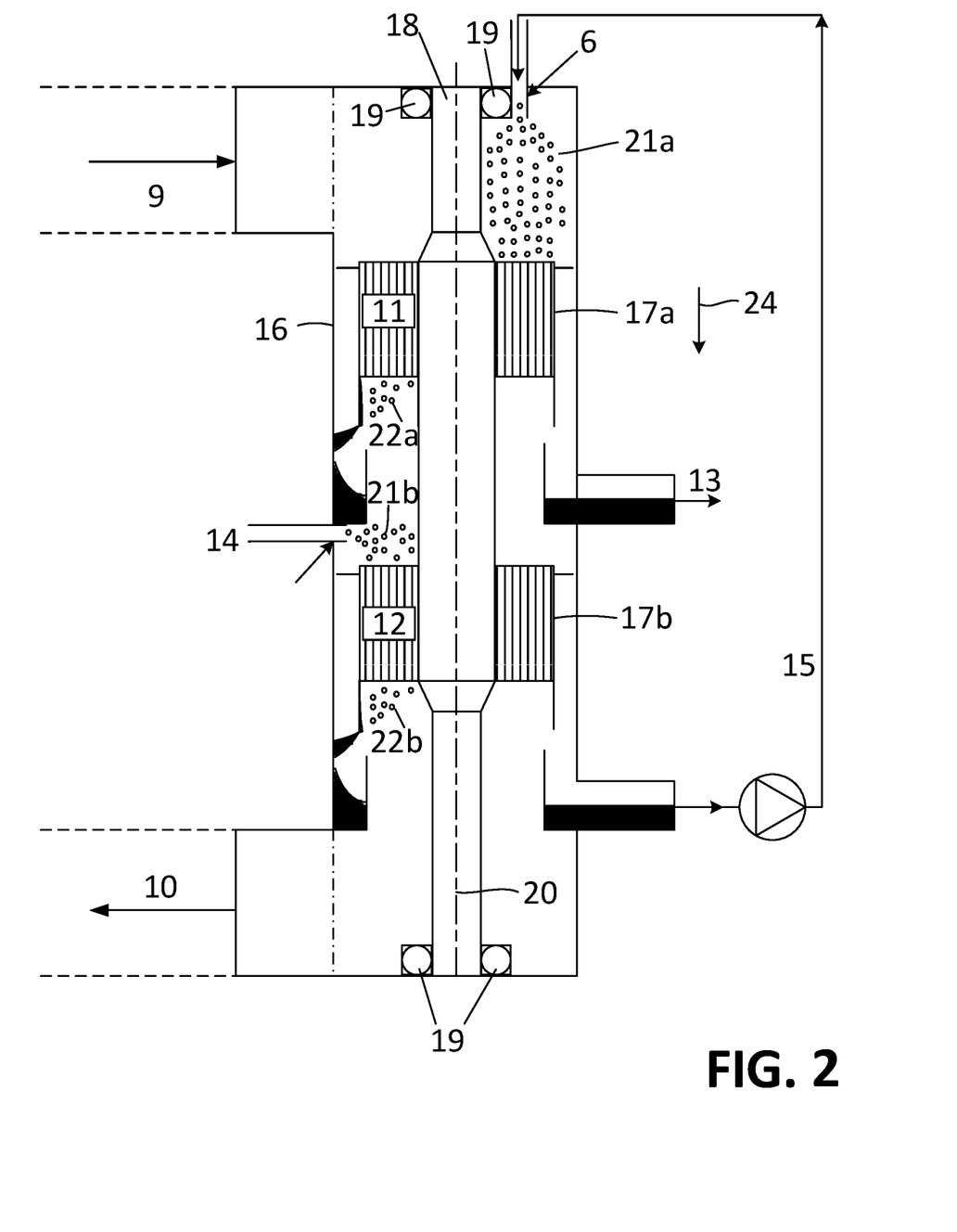
FIG. 2 is a cross-sectional side view of another embodiment of the rotating absorber device according to the invention.

Because of the small cross-sectional width of the channels 1, the gas will exert a rather strong shear force on the liquid 21 while travelling down the rotor 17 form the upstream end to the downstream end. This will cause the liquid 21 to flow in the same (downstream) direction 24 as the gas. To improve the efficiency of the scrubbing operation, and referring to FIG. 2, an embodiment of the rotational absorber device 100 may comprise a first absorbent liquid inlet 6 for absorbent liquid 21a, and a second absorbent liquid inlet 14 for absorbent liquid 21b, located upstream of a first rotor 17a and a second rotor 17b respectively, both provided on a common shaft 18. A first absorbent liquid outlet 13 is provided at a downstream end of the first rotor 17a, whereas a second absorbent liquid outlet 15 is provided downstream of the second rotor 17b, which outlet 15 reconnects to the first inlet 6. The gas enters the device 100 tangentially at the top of the device 100 at inlet 9, and leaves the device 100 at the bottom through outlet 10. The rotating rotors 17a and 17b have been mounted on a common shaft 18 at a top end 11 and a bottom end 12. The rotors 17a and 17b are kept at an axial distance from each other to enable the provision of outlets 13 for removing liquid exiting from the first rotor 17a, and to inject fresh liquid 21b through inlets 14 to an upstream end of the second rotor 17b. The gas exiting the first rotor 17a enters the second rotor 17b, while fresh absorbent liquid 21b is fed through inlet 14 to the second rotor 17b. When leaving the second rotor 17b, the partly used absorbent liquid is returned to the first rotor 17*a* and leaves this rotor 17*a* as more completely or even fully utilized absorbent liquid 22*b*.

The amount of rotors mounted in series on an optionally common shaft may be extended to more than two in order to approximate the configuration of countercurrent absorption in more detail. It is possible therefore to adopt a rotational absorber device that comprises at least two rotors in series, more preferably at least three rotors in series, and even more preferably at least five rotors in series.

Figure 3:
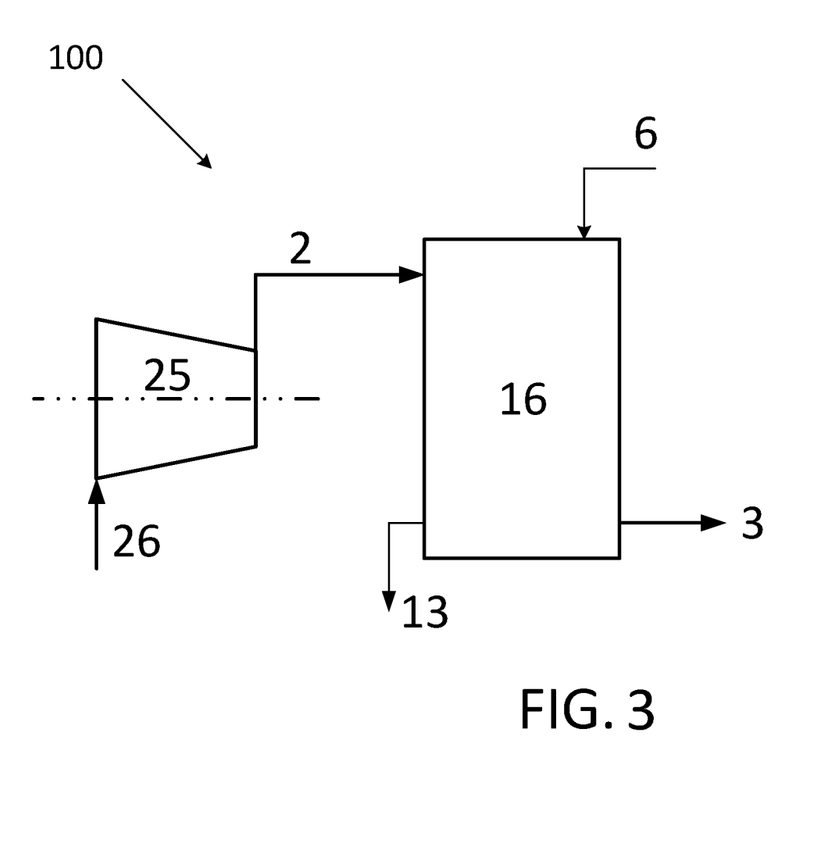
FIG. 3 is a schematic side view of yet another embodiment of the rotating absorber device according to the invention.

A third embodiment of a rotational absorber 100 is shown in FIG. 3. The gas pressure of an incoming gas flow 26 is increased by compression means in the form of a compressor 25 and the pressurized gas enters via gas inlet 2 the housing 16 of the rotor of the rotational absorber 100 according to the invention. Fresh scrubbing fluid or absorbent liquid enters the housing 16 via inlet 6 to remove a contaminant in the gas. Cleaned gas leaves via gas outlet 3 and utilized absorber fluid via outlet 13. The compressor 25 is used to establish a turbulent flow in the scrubbing channels of the rotor of the rotational absorber 100.

Figure 4A:
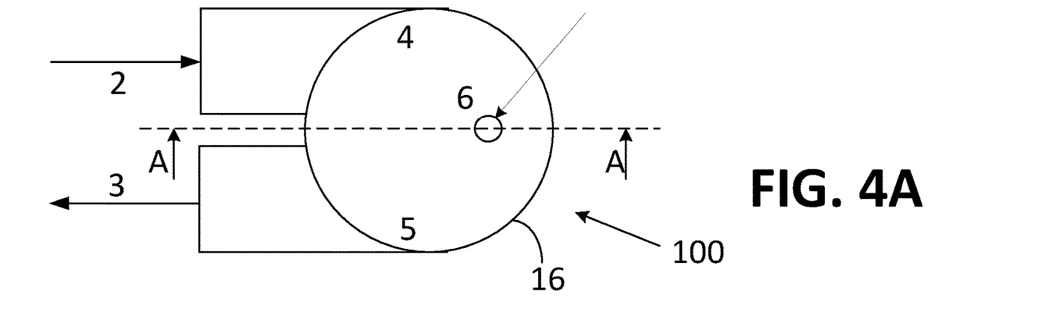
FIG. 4A is a schematic top view of a rotating absorber device according to another embodiment of the present invention.
Figure 4B:
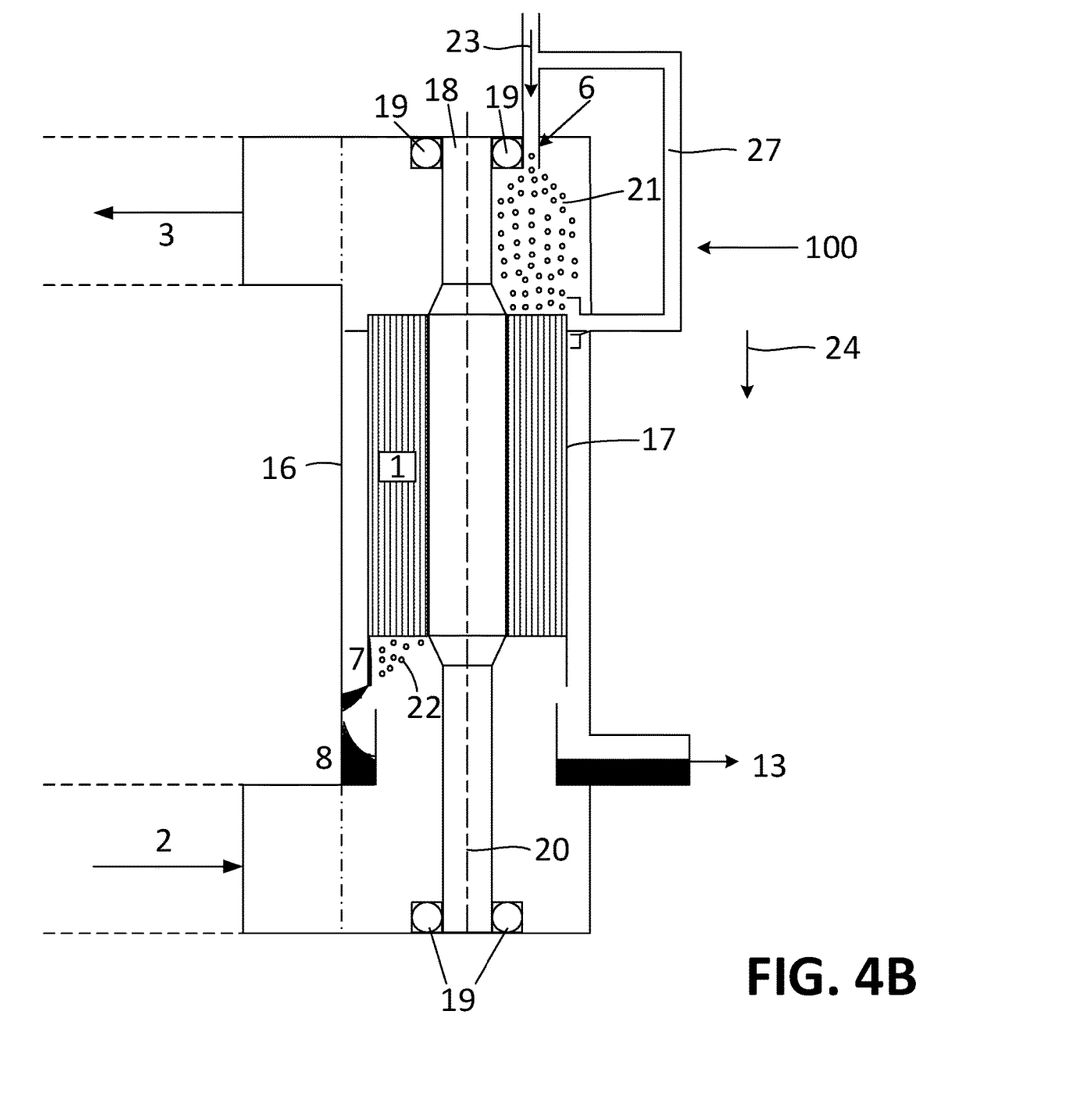
FIG. 4B is a schematic cross-sectional side view of a cross-section along a plane A-A of the embodiment shown in FIG. 4A.

Referring to FIGS. 4A and 4B, a rotating absorber device 100 according to yet another embodiment of the invention is shown. The device 100 is similar to the embodiment shown in FIGS. 1A and 1B except for two differences. First, the housing 16 is provided with a gas inlet 2 that consists of a duct, tangentially positioned at position 4 in the cylindrical housing 16 at a downstream end thereof to induce a swirling rotational motion of the incoming gas in the housing 16. The gas outlet configuration 3 is a mirror image of the gas inlet configuration 2 and comprises a duct that is tangentially positioned at position 5 in the cylindrical housing 16 at an upstream end thereof to direct the outcoming gas from a swirling rotational motion into a translating motion while leaving the housing 16 at position 5.

As with the embodiment of FIGS. 1A and 1B, an inlet 6 for (fresh) absorbent liquid 21 is provided on top of the housing 16 at the upstream end thereof. At the downstream side of the rotor 17, the absorber liquid 21 that now contains absorbate (denoted as absorbate-containing liquid 22) leaves the facing wall of a cylindrical shell 7 that forms an axial extension of the outer boundary wall of the rotor 17. At an inner side of the cylindrical shell 7 wall, a new film of absorbate-containing liquid 22 forms that breaks up at an outer end of the cylindrical shell 7 wall and is propelled as droplets to a liquid collection chamber 8 in the form of a cylindrical ridge provided inside the housing 16. The absorbent liquid leaves the housing 16 at outlet 13.

The embodiment of FIGS. 4A and 4B allows a countercurrent operation of the scrubbing device by injecting absorbent liquid at the top (upstream end) of the device which flows downward while gas which is injected at the bottom (downstream end) of the device flows upward. A fan may be provided to impose a pressure difference and assist the gas flow. Scrubbed gas leaves the rotating element at the top and liquid loaded with absorbate leaves at the bottom.

A second difference between the embodiment of FIGS. 1A and 1B, and that of FIGS. 4A and 4B is that the latter comprises a return conduit 27 for overflow of absorbent liquid. The return conduit 27 connects to the housing 16 at an upward end of the rotor 17 and to the inlet 6 provided on top of the housing 16 at the upstream end thereof. Overflowing absorbent liquid is returned to the inlet 6 through the conduit 27.

Overflow of absorbent liquid may occur when operating the device in counter-current and turbulent conditions, as explained below. Turbulent gas flow in the channels will prevail when the Reynolds number is sufficiently large. For practically realistic values of flow velocity and channel diameter, a pressure in the channels of 2, 3, 4 and up to 5 bar may be needed to have a sufficiently large value of the gas density to end up with turbulent flow. At increased pressure and density combined with turbulent flow, the shear force acting by the upward streaming gas on the liquid film formed in the channels will be large to the extent that gas and liquid flow may flow in the same direction, i.e. both upwards. Even when the channels are oriented in a vertical direction, the force of gravity acting on the absorbent liquid in the channels may not be large enough to result in a downward flow of absorbent liquid opposite to the upward flow of gas. Counter-current flow in the channels may even be impossible in certain cases. On the other hand, at more moderate pressures of below 5 bar for instance, more preferably below 4, bar, even more preferably below 3 bar and most preferably below 2 bar, the upward gas flow is prevailingly laminar and the shear force exerted by the upward streaming gas on the absorbent liquid film in the channels may no longer exceed the force of gravity.

The rotating absorber device may be applied to remove unwanted gaseous constituents from a gas. An example is scrubbing residual gaseous methanol that is present in the gas stream of a methanol-producing plant. The amount of gaseous methanol is typically 0.8% in a gas stream of 45 Nm$^3$/s at 55 bar and ambient temperature. The rotational absorber device 100 reduces the concentration of methanol to 0.04% using water as absorbent liquid at a rate of 2l/s sprayed on top of a rotor 17 rotating at 800 revs/minute in the configuration shown in FIG. 1. The rotor 17 comprises 45000 capillary cylindrical channels 1 of 1.8 mm diameter, and wall thickness of 0.1 mm, braised together in a cylindrical shell of 0.45 in diameter with an axial length of 0.35 in.

The rotational absorber device according to the invention serves as an improvement over conventional scrubbing devices and methods based on spray towers and wet columns, that are frequently used in industry. Non-limiting examples of applications for the present invention include scrubbing of gases containing CO2, ammonia, water vapor, methanol, SO2, H2S, and the like. The invented device has favorable dimensions and operational conditions for removing gaseous contaminants from relatively small gas outlets and for indoor gas cleaning. The device may also be used for scrubbing of SO2 from flue gasses. The relatively small size of the invented device is particularly advantageous for application on vessels and for other marine applications.

The invention claimed is:

1. A rotational absorber device for scrubbing an absorbate from a gas, the device comprising:
    a housing having a gas inlet;
    a gas outlet;
    at least one absorbent liquid inlet;
    means for providing a sustained flow of absorbent liquid to the at least one absorbent liquid inlet; and
    at least one absorbent liquid outlet;
    at least one rotor mounted for rotation in said housing and fluidly connecting to the inlets and outlets, the at least one rotor comprising a plurality of scrubbing channels extending axially and parallel to a common central axis of rotation, wherein the channels are circumferentially enclosed by walls over an entire axial length of the at least one rotor, the at least one rotor being disposed between the at least one absorbent liquid inlet and the at least one absorbent liquid outlet;
    wherein the device further comprises:

means for rotating the at least one rotor causing an absorbent liquid fed to the at least one rotor to be at least partly separated from a gas fed to the rotor, and exit the at least one rotor in the form of absorbent liquid droplets that are propelled radially outwards with respect to the common central axis of rotation of the at least one rotor towards the at least one absorbent liquid outlet where the absorbent liquid is discarded; and wherein the gas inlet and the at least one absorbent liquid inlet are located on one side of the at least one rotor, and the gas outlet and the at least one absorbent liquid outlet are located on an opposite side of the at least one rotor.

2. The rotational absorber device according to claim 1, wherein the axial length of the at least one rotor and the scrubbing channels ranges from 100-5000 times the cross-sectional width of the channels.

3. The rotational absorber device according to claim 1, further comprising pressurizing means adapted to increase the pressure of an inlet gas.

4. The rotational absorber device according to claim 1, wherein the plurality of scrubbing channels amounts to at least 10.

5. The rotational absorber device according to claim 1, further comprising an absorbent liquid collector that connects to the at least one absorbent liquid outlet.

6. The rotational absorber device according to claim 1, wherein the at least one rotor comprises a first rotor and a second rotor both mounted for rotation in said housing and disposed between the at least one absorbent liquid inlet and the at least one absorbent liquid outlet, whereby the second rotor is provided closer to the at least one absorbent liquid outlet axially than the first rotor.

7. The rotational absorber device according to claim 4, wherein the at least one absorbent liquid inlet comprises a first absorbent liquid inlet and a second absorbent liquid inlet, and the at least one rotor comprises a first rotor and a second rotor, the absorbent liquid inlets each being located at an upstream side of the a respective rotor, and wherein the at least one absorbent liquid outlet comprises a first absorbent liquid outlet and a second absorbent liquid outlet, the absorbent liquid outlets each being located at a downstream side of a respective rotor.

8. The rotational absorber device according to claim 7, wherein at least one of the first absorbent liquid outlet and the second absorbent liquid outlet reconnects to at least one of the first absorbent liquid inlet and the second absorbent liquid inlet.

9. A vessel provided with the rotational absorber device according to claim 1.

10. A method for scrubbing an absorbate from a gas, the method comprising providing a rotational absorber device in accordance with claim 1, feeding the gas to the gas inlet, selecting the absorbent liquid by the ability of the absorbate to dissolve in the absorbent liquid, feeding a sustained flow of the absorbent liquid to the at least one absorbent liquid inlet, rotating the at least one rotor in said housing which causes the absorbent liquid to be confined to an inward facing wall of the scrubbing channels and form a film thereto, allowing molecular transport of absorbate from the gas to the absorbent liquid, causing the absorbent liquid fed to the at least one rotor to be at least partly separated from the gas fed to the at least one rotor and exit the at least one rotor in the form of absorbent liquid droplets that are propelled radially outwards with respect to the common central axis of rotation of the at least one rotor towards the at least one absorbent liquid outlet, and exiting the gas through the gas outlet and the absorbent liquid through the at least one absorbent liquid outlet.

11. The method according to claim 10, wherein the absorbate comprises methanol.

\* \* \* \* \*

UNITED STATES PATENT AND TRADEMARK OFFICE
CERTIFICATE OF CORRECTION

PATENT NO. : 11,298,650 B2
APPLICATION NO. : 16/614031
DATED : April 12, 2022
INVENTOR(S) : Jozef Johannes Hubertus Brouwers It is certified that error appears in the above-identified patent and that said Letters Patent is hereby corrected as shown below:

In the Claims

Column 12, Line 2, Claim 7, delete "the a" and insert -- a --

Signed and Sealed this
Ninth Day of August, 2022

*Katherine Kelly Vidal*

Katherine Kelly Vidal
*Director of the United States Patent and Trademark Office*